United States Patent
McNeel et al.

(10) Patent No.: US 9,339,538 B2
(45) Date of Patent: *May 17, 2016

(54) BYSTANDER IMMUNE SUPPRESSION AS A PREDICTOR FOR RESPONSE TO A VACCINE

(71) Applicant: WISCONSIN ALUMNI RESEARCH FOUNDATION, Madison, WI (US)

(72) Inventors: Douglas G. McNeel, Madison, WI (US); William J. Burlingham, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 125 days.

This patent is subject to a terminal disclaimer.

(21) Appl. No.: 14/098,679

(22) Filed: Dec. 6, 2013

(65) Prior Publication Data

US 2014/0161818 A1 Jun. 12, 2014

Related U.S. Application Data

(63) Continuation of application No. 13/343,975, filed on Jan. 5, 2012, now Pat. No. 8,603,485.

(60) Provisional application No. 61/429,944, filed on Jan. 5, 2011.

(51) Int. Cl.
| | |
|---|---|
| *A61K 39/395* | (2006.01) |
| *A61K 39/00* | (2006.01) |
| *C07K 16/22* | (2006.01) |
| *C07K 16/24* | (2006.01) |
| *C07K 16/28* | (2006.01) |

(52) U.S. Cl.
CPC ......... *A61K 39/3955* (2013.01); *A61K 39/0011* (2013.01); *C07K 16/22* (2013.01); *C07K 16/244* (2013.01); *A61K 2039/53* (2013.01); *A61K 2039/55544* (2013.01)

(58) Field of Classification Search
None
See application file for complete search history.

(56) References Cited

U.S. PATENT DOCUMENTS 8,603,485 B2 * 12/2013 McNeel et al. ............ 424/184.1

FOREIGN PATENT DOCUMENTS

WO 2010059975 A2 5/2010

OTHER PUBLICATIONS

Becker, et al., DNA Vaccine Encoding Prostatic Acid Phosphatase (PAP) Elicits Long-Term T-cell Responses in Patients With Recurrent Prostate Cancer, J. Immunother, 2010, 33(6):639-647.
Bobadilla, et al., Th-17, Monokines, Collagen Type V, and Primary Graft Dysfunction in Lung Transplantation, Am. J. Respir. Crit. Care Med., 2008, 177:660-668.
Bradford, et al., Cancer Immunomics: Using Autoantibody Signatures in the Early Detection of Prostate Cancer, Urologic Oncology: Seminars and Original Investigations, 2006, 24:237-242.
Brinkmann, et al., Novel Genes in the PAGE and GAGE Family of Tumor Antigens Found by Homology Walking in the dbEST Database, Cancer Research, 1999, 59:1445-1448.
Burlingham, et al., Mouse Strain and Injection Site are Crucial for Detecting Linked Suppression in Transplant Recipients by Trans-Vivo DTH Assay, American Journal of Transplantation, 2007, 7:466-470.
Cai, et al., Minor H Antigen HA-1-specific Regulator and Effector CD8+ T Cells, and HA-1 Microchimerism, in Allograft Tolerance, J. Exp. Med., 2004, 199(7):1017-1023.
Chen, et al., Induction of CD8+ T Cell Responses to Dominant and Subdominant Epitopes and Protective Immunity to Sendai Virus Infection by DNA Vaccination, Journal of Immunology, 1998, 160:2425-2432.
Cho, et al., Immunostimulatory DNA-Based Vaccines Induce Cytotoxic Lymphocyte Activity by a T-Helper Cell-Independent Mechanism, Nature Biotechnology, 2000, 18:509-514.
Derks, et al., Dendritic Cell Type Determines the Mechanism of Bystander Suppression by Adaptive T Regulatory Cells Specific for the Minor Antigen HA-1, Journal of Immunology, 2007, 179:3443-3451.
Geissler, et al., Human Liver Allograft Acceptance and the "Tolerance Assay": In Vitro Anti-Donor T Cell Assays Show Hyporeactivity to Donor Cells, But Unlike DTH, Fail to Detect Linked Suppression, Transplantation, 2001, 72 (4):571-580.
Hayney, et al., Lung Transplant Patients' T Cell Responses to Influenza Vaccine Viruses Between Seasons, Vaccine, 2008, 26:2596-2600.
Huang, et al., Structural Chemistry and Therapeutic Intervention of Protein-Protein Interactions in Immune Response, Human Immunodeficiency Virus Entry, and Apoptosis, Pharmacology & Therapeutics, 2000, 86:201-215.
Iwasaki, et al., The Dominant Role of Bone Marrow-Derived Cells in CTL Induction Following Plasmid DNA Immunization at Different Sites, Journal of Immunology, 1997, 159:11-14.
Jankowska-Gan, et al., Successful Reduction of Immunosuppression in Older Renal Transplant Recipients Who Exhibit Donor-Specific Regulation, Transplantation, 2009, 88(4):533-541.
Knechtle, et al., Early and Limited Use of Tacrolimus to Avoid Rejection in an Alemtuzumab and Sirolimus Regimen for Kidney Transplantation: Clinical Results and Immune Monitoring, American Journal of Transplantation, 2009, 9:1087-1098.
McNeel, et al., Immunization with Recombinant Human Granulocyte-Macrophage Colony-Stimulating Factor as a Vaccine Adjuvant Elicits Both a Cellular and Humoral Response to Recombinant Human Granulocyte-Macrophage Colony-Stimulating Factor, Blood, 1999, 93(8):2653-2659.
McNeel, et al., Safety and Immunological Efficacy of a DNA Vaccine Encoding Prostatic Acid Phosphatase in Patients with Stage D0 Prostate Cancer, Journal of Clinical Oncology, 2009, 27(25):4047-4054.
Ruiz, et al., Suppressive Immunization with DNA Encoding a Self-Peptide Prevents Autoimmune Disease: Modulation of T Cell Costimulation, Journal of Immunology, 1999, 162:3336-3341.

(Continued)

*Primary Examiner* — Ilia Ouspenski
(74) *Attorney, Agent, or Firm* — Quarles & Brady LLP

(57) ABSTRACT

The present invention relates to antigen-specific immune regulatory response. Methods for detecting an antigen-specific immune regulatory response, methods for selecting candidate vaccine recipients, and methods for improved vaccination strategies are presented.

5 Claims, 8 Drawing Sheets

(56) References Cited

OTHER PUBLICATIONS

Thomson, et al., Delivery of Multiple CD8 Cytotoxic T Cell Epitopes by DNA Vaccination, Journal of Immunology, 1998, 160:1717-1723.

Vanbuskirk, et al., Human Allograft Acceptance is Associated with Immune Regulation, J. Clin. Invest., 2000, 106:145-155.

Xu, et al., Human CD4+CD25low Adaptive T Regulatory Cells Suppress Delayed-Type Hypersensitivity During Transplant Tolerance, Journal of Immunology, 2007, 178:3983-3995.

Merriam-Webster On-Line Dictionary, Definition of Suppress, Accessed by Examiner in U.S. Appl. No. 13/343,975, on Mar. 23, 2013, 2 pages.

PCT International Search Report and Written Opinion, PCT/US2012/020283, Apr. 18, 2012, 13 pages.

European Patent Office, Examination Report, EP12701197.1, Apr. 11, 2014, 25 pages.

Theoret, Marc R., et al. "Phase I Trial of an Enhanced Prostate-Specific Antigen—Based Vaccine and Anti—CTLA-4 Antibody in Patients with Metastatic Androgen-Independent Prostate Cancer." Clinical genitourinary, cancer 5.5 (2007): 347-350.

European Patent Office, Examination Report, EP127011971.1, May 29, 2015, 8 pages.

* cited by examiner

FIG. 1A-D

FIG. 3A and B

FIG. 4A-C

FIG. 6A
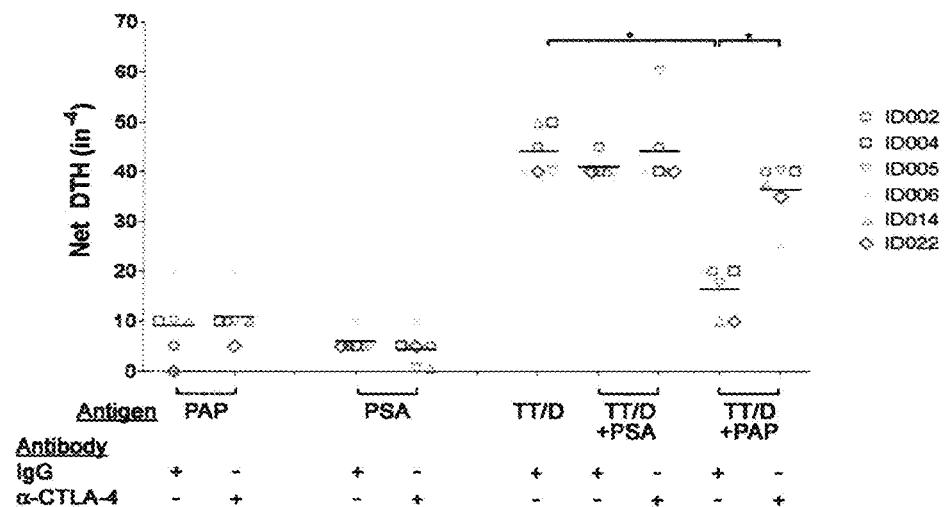
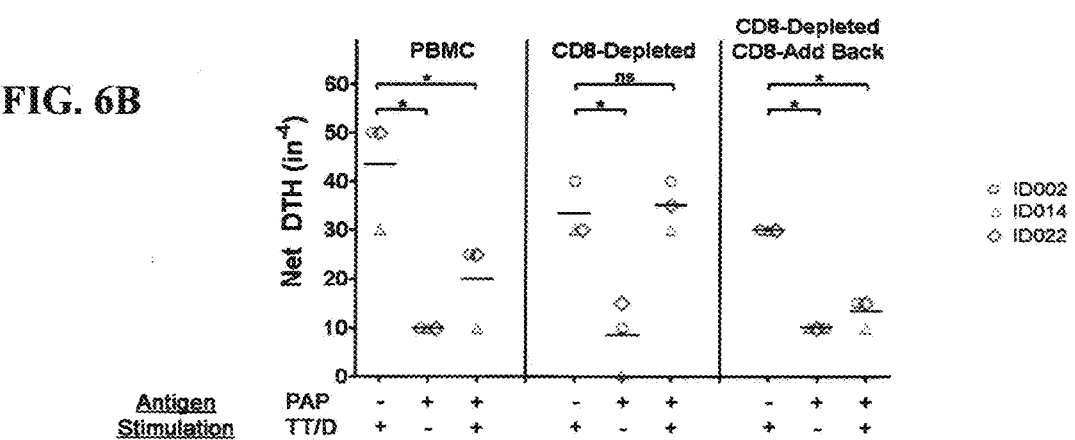
FIG. 6B
FIG. 6C
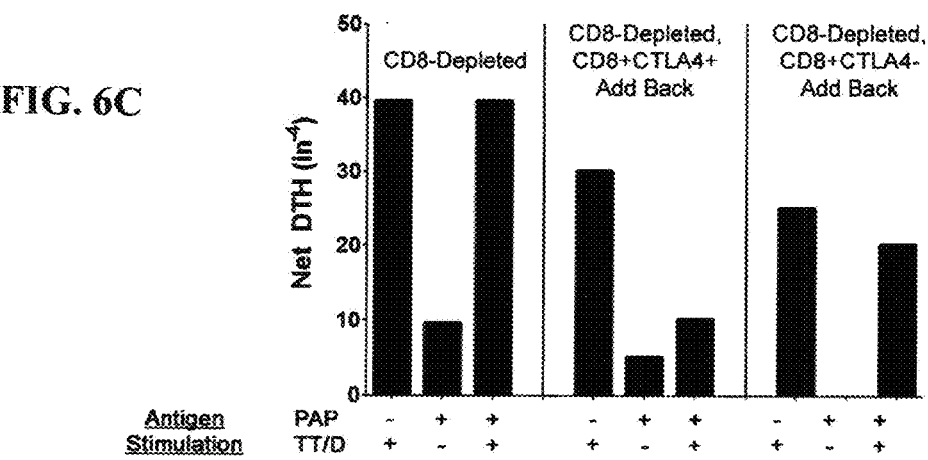

FIG. 7A-C
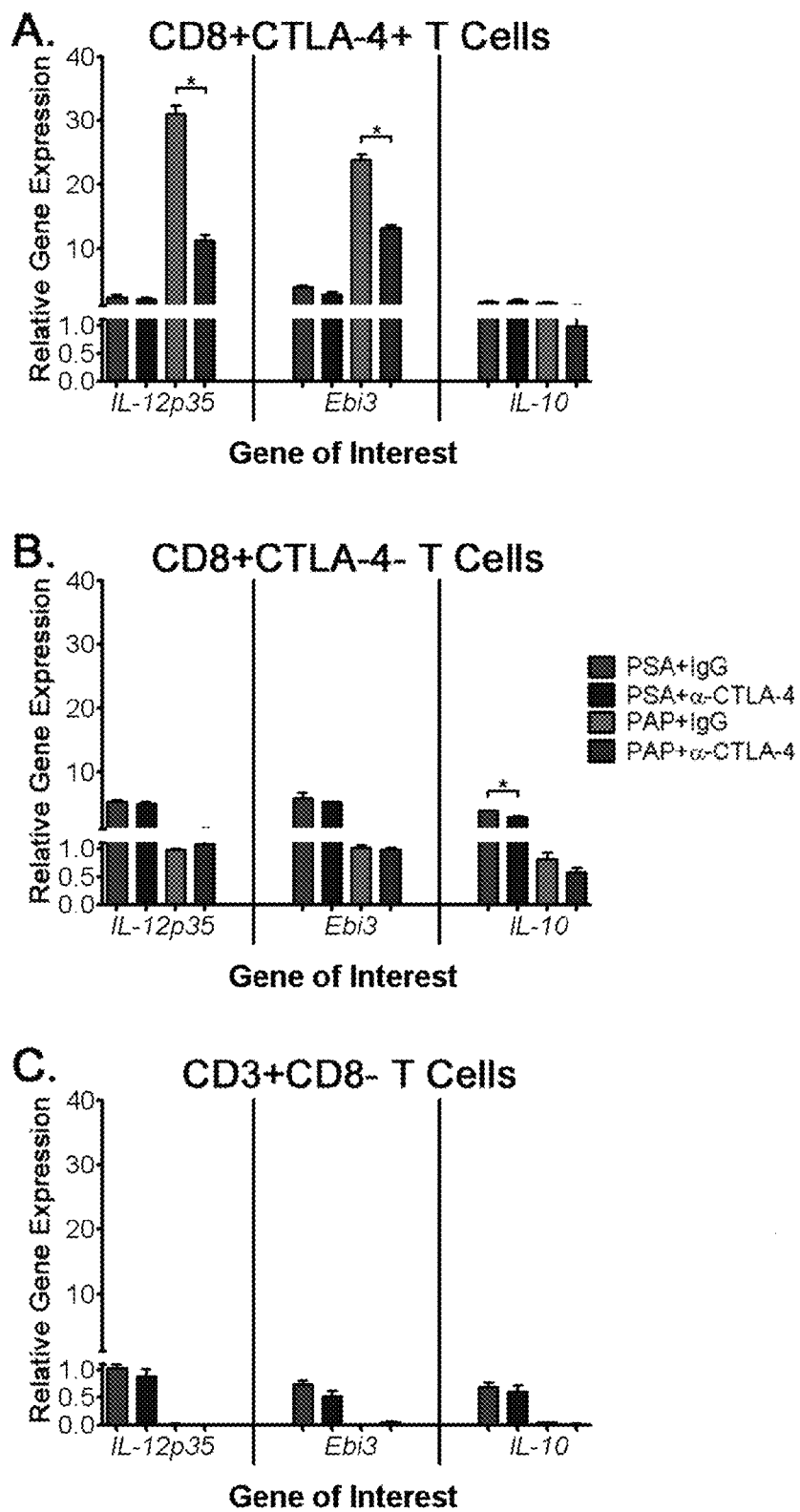

BYSTANDER IMMUNE SUPPRESSION AS A PREDICTOR FOR RESPONSE TO A VACCINE

CROSS-REFERENCE TO RELATED APPLICATIONS

This application is a continuation application of U.S. application Ser. No. 13/343,975, filed Jan. 5, 2012, which claims the benefit of U.S. Provisional Patent Application No. 61/429,944, filed Jan. 5, 2011, each of which is incorporated herein by reference in its entirety.

STATEMENT REGARDING FEDERALLY SPONSORED RESEARCH OR DEVELOPMENT

This invention was made with government support under W81XWH-05-1-0404 awarded by the US ARMY/MRMC and RR016489 and CA142608 awarded by the National Institutes of Health. The government has certain rights in the invention.

BACKGROUND

Vaccines that elicit an antigen-specific T cell response to diseased cells harbor great promise (Pavlenko et al., Expert review of vaccines 2005; 4(3):315-327). Because of the inherent risks and high cost of certain vaccines, such as cancer vaccines directed at cells expressing a cancer antigen, there is a great need to identify individuals likely to benefit from cancer vaccination. However, efficient methods for assessing in advance of vaccine administration whether an individual will respond to a particular vaccine were not available prior to the inventors' work.

Cancer vaccines are based on the premise that certain antigens are expressed on cancerous cells but not, or in smaller amounts, on healthy cells. To elicit an immune response against cancerous cells expressing the antigen, the cancer antigen is delivered to an individual, e.g., as protein or nucleic acids encoding a gene for the antigen. The antigen is then processed and presented on antigen-presenting and other cells through MHC class I molecules thereby eliciting a CD8+ cytolytic T cell response directed at cancer cells expressing the antigen (Iwasaki et al., J. Immunol 1997; 159 (1):11-14; Chen et al., J. Immunol. 1998; 160(5):2425-2432)). The immune system of an individual vaccinated with a cancer antigen would, thus, eliminate cancerous cells expressing the antigen.

In practice, administration of an antigen for vaccination does not always follow the process outlined above because antigen exposure can also result in antigen-specific immunological tolerance, i.e., non-responsiveness (Kang et al., 2007; 353(4): 1034-1039; Ruiz et al., J. Immunol. 1999; 162(6): 3336-41). For example, in rats, repetitive administration of DNA vaccines is necessary to elicit detectable T-cell responses for an autologous antigen (Johnson, et al., Cancer Immunol. Immunother. 2007; 56(6):885-95). Similarly, multiple immunizations appeared necessary to detect PAP-specific T cells in human patients with prostate cancer (Becker et al., J. Immunol. 2010:(in press)). Likewise, frequent administration of a plasmid DNA encoding myelin basic protein resulted in better clinical outcome for individuals with relapsing-remitting multiple sclerosis, a disease mediated by an inflammatory-type immune response.

The fact that administering an antigen can both elicit or suppress immunity, has raised serious concern. For example, administration of a DNA plasmid for inducing tolerance to self antigens could induce or exacerbate autoimmunity Conversely, treatment with plasmid DNA for mounting an anti-cancer immune response could result in unwanted tolerance to certain cancer antigens (Johnson et al., Vaccine 2006; 24:293-303). Further, when both an effector and a suppressive immune response is mounted in an individual, the effect of DNA administration to induce immunity might not be phenotypically apparent. For example, during a Phase I clinical trial, several individuals with early recurrent prostate cancer that received six biweekly immunizations with a DNA vaccine encoding prostatic acid phosphatase (PAP) developed PAP-specific effector CD4+ and CD8+ T-cells (McNeel et al., Oncol. 2009; 27(25):4047-4054). In some individuals, these responses were detected shortly after immunization and persisted for several months after immunization. However, in some individuals, a response could not be detected until several months after completing an initial immunization series (Becker et al., J. Immunother. 2010; 33(6) 639-647). The underlying mechanism for these differences in response is unknown.

Delayed-type hypersensitivity (DTH) is a cell-mediated response of the immune system to foreign antigens. For several decades, testing for DTH has been a standard means of evaluating pre-existing cellular immunity to antigens (Hersh et al., Ann. N.Y. Acad. Sci. 1976; 276:386-406). DTH testing is used routinely in the clinical evaluation of prior exposure to agents such as tuberculosis or tetanus, and is associated with other in vitro measures of T-cell immunity, such as T-cell proliferation, Th1-type cytokine bias, and cytolytic T-cells (Gordon et al., J. Allergy Clin. Immunol. 1983; 72(5 Pt 1):487-94., Dietert et al., J. Immunotox. 2008; 5(4):401-12). Loss of DTH response to common antigens has also been used as a standard test for immunosuppression (Huebner et al., Clin. Infect. Dis. 1994; 19(1):26-32).

In recent years, DTH testing has been used to evaluate T-cell responses following immunization with antigen-specific vaccines, particular peptide-based vaccines. For example, a DTH response to immunization with a polyvalent cell-based melanoma vaccine was an independent predictor of clinical outcome (Hsueh et al., J. Clin. Oncol. 1998; 16(9): 2913-20). DTH testing has limitations, however, and its use is not always practical or possible. For example, DTH testing of DNA vaccines requires production of separate good manufacturing practice-grade antigens. Also, information derived from the DTH test, i.e., area of induration and erythema, does not necessarily provide mechanistic information because a DTH response can be mediated by multiple factors. DTH responses at the site of immunization do not always indicate an immune response to the administered antigen but, instead, might indicate a response to a vaccine adjuvant, such as the cytokine adjuvant GM-CSF commonly used in anti-cancer antigen vaccines, confounding the interpretation of these results (McNeel et al., Blood 1999; 93(8):2653-9).

DTH can also be assessed trans vivo, i.e., by measuring a swelling response in another organism (vanBuskirk et al., J. Clin. Invest. 2000; 106:145-155). For this trans vivo DTH (TV-DTH) assay, peripheral blood mononuclear cells (PBMC) from an individual and an antigen of interest are administered intradermally to an animal, such as into the footpad or ear of a mouse having severe combined immunodeficiency (SCID). The presence of a DTH response is then determined by measuring footpad or ear swelling 24 hours after administration of the cells and the antigen. The TV-DTH assay has been used to evaluate the immune response to target tissue antigens following solid organ transplantation, e.g., to monitor the immune response of renal allograft recipients (Knechtle et al., Am. J. Transpl. 2009; 9:1087), and to investigate mechanisms of tolerance induction (Geissler et al., Transplantation 2001; 72(4): 571-80).

Thus, there remains a great need in the art for reliable methods to identify individuals that are likely to benefit from vaccination as well as for methods of improving successful elicitation of a cancer antigen-specific immune response in response to DNA vaccination.

BRIEF SUMMARY

The invention is based on the observation that some individuals exhibit an antigen-specific suppressive immune response that suppresses an anti-cancer antigen effector response. It was not known in the art that certain individuals evidence a "baseline" cancer-antigen-specific suppressor immune response. It was further unknown that the presence of such baseline suppressive immune function can predict successful DNA vaccination and, thus, can be used as indicator for selecting vaccination candidates.

The invention relates generally to cancer antigen-specific suppressive immunity of an individual prior to and following vaccination.

In a first aspect, the present invention is summarized as a method for determining cancer antigen-specific suppressive immunity. The method includes administering to an animal peripheral blood mononuclear cells from an individual and a target cancer antigen. The animal is then inspected for a delayed-type hypersensitivity response to the cancer antigen mediated by the administered cells.

In some embodiments of the first aspect, the individual has not previously received a vaccine to the target antigen.

In some embodiments of the first aspect, the peripheral blood mononuclear cells and the target antigen are administered at the same time.

In some embodiments of the first aspect, the peripheral blood mononuclear cells and the target antigen are administered by injection into a footpad of the animal. According to this specific embodiment, the thickness of the footpad can be measured prior to and following administration of the cells to determine if the injected cells gave rise to DTH in response to the target antigen.

In a second aspect, the present invention is summarized as a method for enhancing vaccine-mediated immunity in an individual by administering the vaccine and an agent that suppresses immune regulatory cell function to the individual.

In some embodiments of the second aspect, the agent is an anti-CTLA-4 antibody, an anti-IL-35 antibody, an anti-TGF beta antibody, or-an anti-IL-10 antibody.

In some embodiments of the second aspect, the vaccine and the agent are administered to the subject at the same time.

In a third aspect, the present invention is summarized as a method of selecting candidate individuals to receive a vaccine. The method includes administering to an animal (a) peripheral blood mononuclear cells from an individual and (b) a target antigen. The animal is then inspected for a delayed-type hypersensitivity response to the target antigen mediated by the administered cells in an assay configured to distinguish between absence of an effector response to the target antigen and presence of an antigen-specific immune regulatory response. Individuals whose cells mediated a delayed-type hypersensitivity response suppressed by the antigen-specific immune regulatory response in the animal are selected as candidates for receiving a vaccine.

In a fourth aspect, the present invention is summarized as a method of monitoring immunological response of an individual having received vaccination. The method includes administering to an animal (a) peripheral blood mononuclear cells from an individual having received a vaccination and (b) an antigen. The animal is then inspected for a delayed-type hypersensitivity response to the antigen mediated by the administered cells.

The methods and compositions described herein are useful in a variety of applications that include candidate selection for vaccination and, more specifically, for anti-cancer vaccination, antigen selection, and improved vaccination strategies.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein:

FIG. 1A illustrates serum PSA levels of patient ID007 who received six biweekly immunizations with a DNA vaccine encoding PAP. The immunization series is indicated by the grey box, and stars indicate peripheral blood sampling for immune monitoring. FIG. 1B illustrates IFNγ ELISPOT responses of PBMC from patient ID007 prior to ("Pre") or two weeks following ("Post") six biweekly immunizations and at three-month intervals thereafter. PBMC were evaluated for IFNγ responses following 48-hour stimulation with media alone (No Ag), PAP, tetanus toxoid (TT/D), or a PHA positive control. Shown are the mean and standard deviation of quadruplicate samples at each time point in spot-forming units (SFU). FIG. 1C illustrates pre- or post-immunization PBMC from three patients (ID005, ID007, and ID014) following injection into the footpads of SCID mice with the indicated antigens (TT/D, PAP, or PSA) and blocking antibodies (IgG control, anti-CTLA-4, anti-TGF-β, or anti-IL-10). DTH swelling responses (in$^{-4}$) were measured after 24 hours. Data shown are representative of two independent experiments. Differences in mean TV-DTH responses between these groups were analyzed using an unpaired student's t-test with * indicating p<0.05. FIG. 1D illustrates post-immunization samples obtained from patients ID005 and ID014 and used in a similar TV-DTH assay in which responses to TT/D alone or in combination with PAP or PSA were measured in the presence or absence of a CTLA-4 blocking antibody. Differences between treatment group mean DTH values were compared using an unpaired student's t-test, with * indicating p<0.05.

FIG. 3A illustrates the net footpad swelling 24 hours after PBMC injection into the footpads of SCID mice with 1-25 µg of the indicated antigens and blocking antibodies or control IgG (1 µg). N.D.=no data.

FIG. 4A illustrates the net footpad swelling 24 hours after PBMC from patients before, or two weeks after, a series of six injections with PAP or tetanus toxoid into the footpads of SCID mice, with or without an antibody specific for CTLA-4 or IgG control. Net DTH responses were determined after 24 hours. FIG. 4B illustrates swelling response mediated by PBMC, PBMC depleted of CD8+ cells, or PBMC depleted of CD8+ cells with purified CD8+ cells added, obtained from the same individual following immunization. Cells were injected into the footpads of SCID mice with the indicated antigens. DTH responses were measured after 24 hours (background subtracted). FIG. 4C illustrates antigen-specific bystander suppression as in FIG. 4B by PBMC from the same patient, obtained after immunization, in the presence or absence of blocking antibody specific for CTLA-4.

FIG. 6A-C illustrate that PAP-specific regulatory cells exist prior to immunization and are CD8+CTLA-4+. FIG. 6A illustrates PBMC samples from multiple prostate cancer patients tested using TV-DTH for pre-existing PAP-specific regulatory responses. PBMC were stimulated with the described antigens and antibody treatments and TV-DTH reactivity was measured. Differences in mean TV-DTH swelling among different antigen/antibody treatment groups (indicated by solid lines) were compared using an unpaired student's t-test, with * indicating p≤0.05. FIG. 6B illustrates PAP-specific regulatory responses evaluated in TV-DTH studies using samples from patients identified in panel A. These studies were conducted using whole PBMC (left section), PBMC samples that had been depleted of CD8+ T-cells (center section), or PBMC samples that had been depleted of CD8+ T-cells and were subsequently supplemented with autologous CD8+ T-cells (right section). Statistical differences between group mean DTH values (indicated by solid lines) were analyzed using an unpaired student's t-test with * indicating p≤0.05. FIG. 6C illustrates PBMC samples from patient ID022 as evaluated for tetanus bystander suppression by TV-DTH. PBMC samples were depleted of CD8+ T-cells and tested alone (left section) or supplemented with magnetic bead-sorted CD8+CTLA-4+ T cells (center section) or CD8+CTLA-4− T-cells (right section) along with the identified antigens.

FIG. 7A-C illustrate that blockade of PAP-specific CD8+ CTLA-4+ regulatory cells decreases their expression of IL-35. Samples from a patient with CTLA-4 regulated PAP-specific immune responses (ID022) were stimulated for 24 hours with PAP, PSA, or media alone in the presence of an anti-CTLA-4 antibody or an IgG control. Cells were then sorted via flow cytometry for the following populations: CD3+CD8+CTLA-4+ (FIG. 7A), CD3+CD8+CTLA-4− (FIG. 7B), or CD3+CD8− (FIG. 7C). Relative mRNA expression of IL-12p35, Ebi3, and IL-10 was determined by quantitative RT-PCR and were normalized against the ribosomal protein P0 as an internal control and the media-alone cell-sorted sample. Differences between control IgG and anti-CTLA-4 treatment group means were calculated using an unpaired student's t-test with * indicating p≤0.05. Data shown is representative of three independent experiments.

Figure 1:
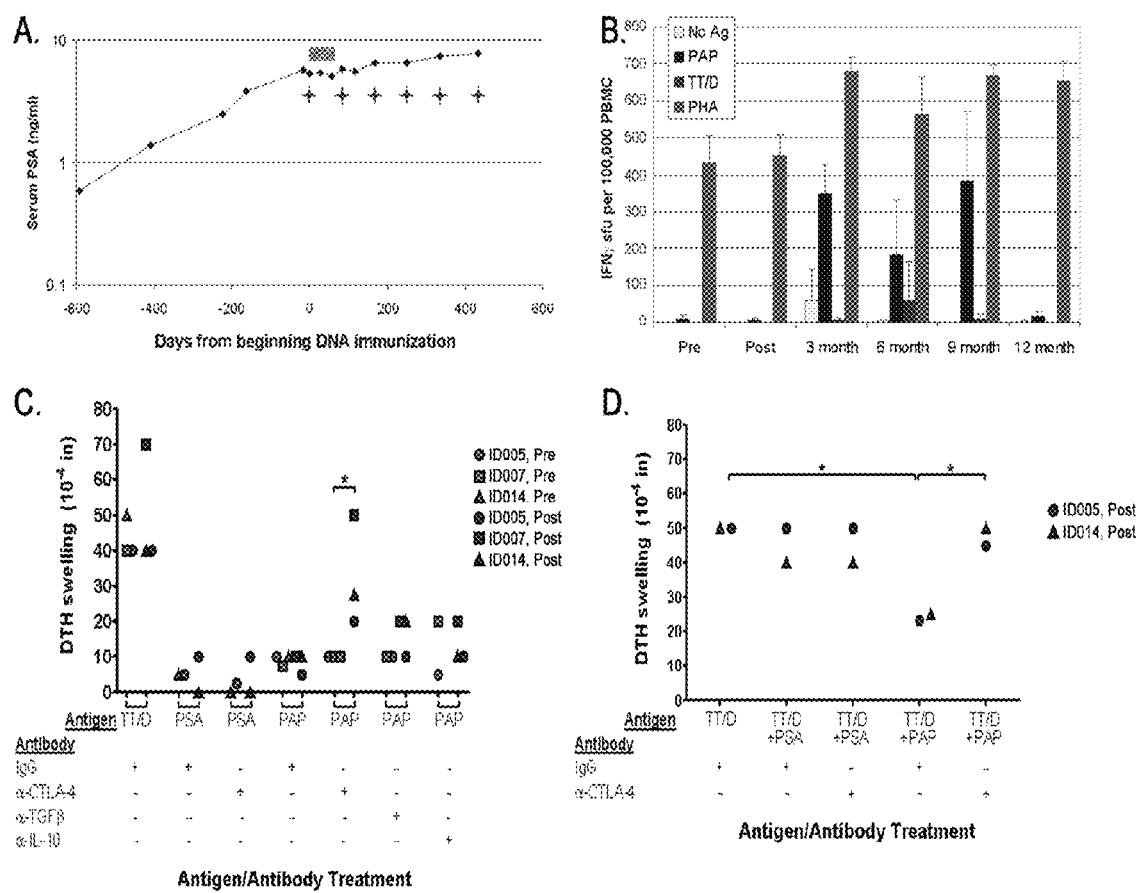
FIG. 1A-D illustrate CTLA-4-dependent suppression of PAP antigen-specific T effector immune responses by PAP-specific T regulatory cells following immunization.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DESCRIPTION OF EXEMPLARY EMBODIMENTS

The invention relates to detecting antigen-specific effector and regulatory responses, prior to or following vaccination, that have not previously been detected. Detection of antigen-specific immune regulatory responses can be used to select suitable individuals for vaccination. The invention also relates to methods for improved immunization strategies, i.e., administering a vaccine with one or more agents that suppress immune regulatory cell function, such as blocking antibodies or receptor antagonists, to enhance immune response to vaccination. The trans vivo DTH (TV-DTH) assay can aid selection and monitoring of individuals likely to immunologically respond to such approach.

The invention relates to the inventors' observation that an immune response to a cancer antigen, such as prostatic acid phosphatase (PAP), following DNA vaccination could not be detected until several months after immunization. This finding prompted inquiry into whether an immune regulatory cell response had suppressed the development of anti-cancer antigen DTH. The TV-DTH assay was used to determine whether cancer antigen-specific immune regulatory cells were present prior to or following immunization with the cancer antigen-specific DNA vaccine.

Antigen-specific immune regulatory cells were detected using this assay following immunization with the DNA vaccine. Moreover, for the first time, antigen-specific immune regulatory cells were detected prior to immunization in several individuals. Thus, some individuals exhibit spontaneous cancer antigen-specific regulatory responses which can mask the function and/or detection of effector immune responses following cancer antigen vaccination.

Antigen-specific immune regulatory responses can vary between antigens. For example, the inventors observed that the examined individuals mounted a suppressive response to PAP but not to PSA, even though both antigens can serve as vaccine targets. However, because antigen-specific regulatory responses also vary between patients, it is conceivable that some individuals can develop suppressive immunity to PSA. Advantageously, the invention can be used to select antigens suitable for vaccination of a particular individual. Without intending to be limited to any particular theory, the inventors believe that individuals having a regulatory immune response to a particular vaccine antigen are more likely to respond to the vaccination because the pre-existing antigen-specific effector response can be expanded by immunization.

The TV-DTH approach has not previously been applied to evaluating suppressive immune responses prior to or following anti-cancer antigen immunization. The TV-DTH model employs footpad or ear swelling in mice or other suitable animals as a measure of immune response. Advantageously, the animal is immunocompromised such that the animal's immune cells do not interfere with interpreting a response by the transferred cells. See, e.g., Burlingham et al., Am J Transplant 2007; 7:466-470. Examples of immunocompromised animals include SCID mice and recombinase-2-deficient mice. Typically, peripheral blood mononuclear cells (PBMCs), which include lymphocytes and monocytes, are isolated from a subject to be tested for DTH, for example, by subjecting a blood sample to Ficoll-density centrifugation. An appropriate number of PBMCs, e.g., 1-10 million, is then injected into the footpads or ears of the animal along with a particular antigen. An antigen can be any substance, molecule, microorganism, or fragments thereof that can bind to cells and/or molecules of the immune system and elicit an immune response. Antigens include proteins, peptides, carbohydrates, nucleic acids, and chemicals. Antigens can be isolated from natural sources or produced and/or modified in the laboratory. Preferably, the recipient mice are "naive" in that they have not previously been injected with PBMCs and antigen. The antigen can be administered together with or separately from the PBMCs. Donor antigens can be prepared from PBMCs or splenocytes and can be used to control for non-DTH-mediated swelling, as explained below. Recall antigens, such as tetanus toxoid or inactivated Epstein-Barr virus, can be any antigen that can be used as a positive control for DTH-mediated swelling.

The cells and antigen can be provided and administered in an appropriate carrier medium, such as buffer, at an appropriate volume, e.g., 5-50 µl. Preferably, cells without the antigen, antigen without PBMCs, PBMCs with a donor antigen, or carrier medium alone, in the same volume are administered to a separate footpad or ear of the same mouse to control for changes in thickness not attributable to DTH.

As used herein, "measuring a DTH response" means determining whether a DTH response occurred and, optionally, to what extent. If swelling is used as a readout for determining if a DTH occurred, then swelling above a certain threshold will be interpreted as indicating DTH. For example, before administering the cells and the antigen, footpad or ear thickness of the mice can be measured, for example, using a dial thickness gauge to obtain a pre-administration measurement. Approximately 12-48 hours post-administration of PBMCs and antigen, the footpad or ear thickness is measured again to obtain a post-administration measurement. Changes in the thickness of the footpad or ear are determined by subtracting the pre-administration measurement from the post-administration measurement.

Administration of cells or antigen alone can produce varying background, i.e., non-DTH, swelling, e.g., $10-20 \times 10^{-4}$ inches for antigen or PBMCs alone. To account for varying background swelling when comparing responses from different individuals or different experiments, i.e., to measure DTH-mediated swelling, the swelling elicited by administration of PBMC or antigen alone can be subtracted from the swelling elicited by administration of both PBMCs and antigen to obtain a normalized swelling response. When swelling responses are normalized to background swelling, swelling less than $10 \times 10^{-4}$ inches is ordinarily considered negative, i.e., no DTH can be detected. Swelling greater than $10 \times 10^{-4}$ inches is ordinarily considered positive. Swelling of $10-20 \times 10^{-4}$ inches can be considered weak DTH responses, $25-35 \times 10^{-4}$ inches can be considered intermediate DTH responses, and $40 \times 10^{-4}$ inches or more can be considered strong DTH responses. These measurements represent general guidelines. A determination of the presence or absence of a DTH response can be made on a case-by-case basis.

If the swelling response is considered negative, the administered cells either did not elicit a DTH or the DTH was suppressed by an immune regulatory response. The invention specifically contemplates measuring the response in an assay configured to distinguish between these two possibilities, i.e., the absence of an effector response to the antigen and the presence of an immune regulatory response. In one exemplary embodiment, the assay distinguishes between these two possibilities by measuring the response to a recall antigen in the presence of the antigen of interest. If the cells mount a response to the recall antigen alone but not to the recall antigen in the presence of the antigen of interest, then an antigen-specific immune regulatory response is present and responsible for the negative swelling response. Conversely, if a response to the recall antigen is unaffected by the presence of the antigen of interest, the negative response can be attributed to an absence of an effector response to the antigen of interest.

In another exemplary embodiment, the assay can be configured to distinguish between absence of an effector and presence of immune regulatory response by administering the antigen with an agent that suppresses immune regulatory cell function. Examples of such agents include agents that suppress the function of CTLA-4, IL-35, TGF-beta, or IL-10, such as blocking antibodies or receptor antagonists. As used herein, "suppress" means to lessen, diminish, or completely abrogate cell function. If the negative swelling response is unaffected by the presence of such agent, the negative response can be attributed to an absence of an effector response to the antigen of interest. If swelling in response to the antigen occurs in the presence (but not the absence) of the agent, however, the negative swelling response can be attributed to an antigen-specific immune regulatory response suppressing the effector response.

Vaccines can elicit antigen-specific effector T cells for anti-cancer treatment. In the case of DNA vaccines, an antigen is delivered to an individual in the form of DNA encoding the antigen, which is subsequently expressed, processed, and presented by antigen-presenting cells through MHC class I and can lead to potent CD8+ cytolytic T cells (Iwasaki et al., J. Immunol. 1997; 159(1):11-14; Chen et al., J. Immunol 1998; 160(5):2425-32; Thomson et al., J. Immunol. 1998; 160(4):1717-23; Cho et al., Nat. Biotechnol. 2000; 18(5): 509-14, each of which is incorporated herein as if set forth in its entirety). DNA vaccines contain at least one gene encoding at least one peptide, protein, or protein fragment. Such gene can be part of a vector, such as a plasmid. The DNA can be packaged in vessels, such as liposomes or administered as "naked DNA." DNA vaccines can be administered to an individual by any suitable method. For example, DNA vaccines can be administered via injection, such as intradermal or intramuscular injection. DNA vaccines can also be administered by using gene gun delivery, i.e., ballistically accelerating DNA that has been absorbed to suitable carrier microparticles. Further administration routes include oral and topical application, such as by exposure to mucosal tissue.

The invention specifically contemplates identifying individuals in need of improved vaccination strategies. Improved vaccination strategies include administering a vaccine and an agent that suppresses immune regulatory cell function to improve immunity conferred by the vaccination. The vaccine and the agent can be administered to the subject at the same time or sequentially. Examples of agents that suppress immune regulatory cell function include agents that block the function of CTLA-4, IL-35, TGF-β, or IL-10, such as blocking antibodies or receptor antagonists. In some cases, an individual may not exhibit a suppressor response immediately following vaccination but, instead, the suppressor response may develop over time. In such cases, it may be advantageous to administer a specific blockade treatment such as administration of an anti-CTLA-4 or anti-IL-35 antibody.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

The invention will be more fully understood upon consideration of the following non-limiting Examples.

EXAMPLE 1

Antigen-Specific Immune Suppression

Patient Populations: Peripheral blood mononuclear cells (PBMC) used for the studies were obtained from individuals previously treated as part of a clinical trial at the University of Wisconsin Carbone Cancer Center. This included 21 subjects with PSA-recurrent prostate cancer, without radiographic evidence of metastases, and not receiving concurrent androgen deprivation. All subjects gave written, IRB-approved consent for the use of residual blood products to be used for immunological research. Pre-immunization PBMC was collected by leukapheresis prior to vaccination with six biweekly intradermal injections of a DNA vaccine encoding PAP. All subjects also received an intramuscular tetanus booster immunization prior to receiving the DNA vaccinations. Post-immunization PBMC were collected by leukapheresis two weeks following the last immunization. All PBMC were cryopreserved in aliquots in liquid nitrogen until use.

Mice: Mice with severe combined immune deficiency (SCID) were bred at the University of Wisconsin Gnotobiotic Laboratory facility. All animals were housed and treated in accordance with guidelines outlined by the University of Wisconsin and the National Institutes of Health, and under an IACUC-approved protocol.

Trans-Vivo Delayed-Type Hypersensitivity (TV-DTH) Assay: $7-9\times10^6$ PBMC obtained from patients prior to and following immunization were co-injected into the footpads of 6- to 8-week old SCID mice with 1 µg of PAP protein (Fitzgerald Industries, Acton, Mass.). The response to tetanus toxoid (TT/D; Aventis Pasteur, Bridgewater, N.J.) recall antigen alone plus PBMC was used as a positive control, and PBMC plus phosphate-buffered saline (PBS) was used as a negative control. Antigen-driven swelling response was determined as described in VanBuskirk et al., J. Clin. Invest. 2000; 106(1):145-55, incorporated herein by reference as if set forth in its entirety. DTH reactivity after 24 hours was measured as the change in footpad thickness in multiples of $10^{-4}$ inches, measured using a dial thickness gauge (Mitutoyo, Japan), and net swelling is the antigen-specific swelling subtracted for the contribution obtained with PBMC plus PBS. To determine the effect of neutralizing antibodies on bystander suppression, PBMC were mixed with 1 µg of PAP antigen and 25 µg of either control IgG or rabbit anti-human TGF-β, goat anti-human IL-10 (R&D Systems, Minneapolis, Minn.), or 1 µg of mouse anti-human CTLA-4 monoclonal antibody (mAb) (AbSolutions, Mountain View, Calif.) and injected into the footpads of SCID mice. Bystander suppression was measured as inhibition of recall antigen response in the presence of PAP antigen or prostate specific antigen (PSA) as a control and calculated as previously described (Derks R A, Jankowska-Gan E, Xu Q, Burlingham W J. Dendritic cell type determines the mechanism of bystander suppression by adaptive T regulatory cells specific for the minor antigen HA-1. J. Immunol 2007; 179(6):3443-51, incorporated herein by reference as if set forth in its entirety). To assay for DTH following stimulation with a control antigen, PBMC were first mixed with 1 µg of PAP antigen and 25 µg of TT/D (tetanus toxoid). Subsequently, 1 µg anti-human CTLA-4 mAb or control IgG was added and the mixture was injected into the footpads of SCID mice. DTH reactivity was again measured after 24 hours as described above. Results are expressed as the change in swelling induced by PBMC and antigen compared to PBMC+PBS alone. For the above-described assays, an absolute net TV-DTH response of $>20\times10^{-4}$ inches and changes in net TV-DTH$>10\times10^{-4}$ inches in response to a particular antigen were considered to be consistent with the presence or gain of a DTH immune response (VanBuskirk et al., J. Clin. Invest. 2000; 106(1):145-55; Cai et al., J. Exp. Med. 2004; 199(7):1017-23; Xu et al., J. Immunol 2007; 178(6):3983-95). In separate experiments, PBMC were depleted of CD8+ T cells by magnetic bead selection (StemCell Technologies, Vancouver, BC), according to the manufacturer's instructions. In these studies, the purity of CD3+CD8+ cells and effective depletion of CD8+ T cells from PBMC was >94%, as determined by flow cytometry.

IFNγ ELISPOT: ELISPOT was performed as previously described by Becker et al., J. Immunother. 33(6):639-647 (2010), incorporated herein by reference as if set forth in its entirety. In brief, wells of nitrocellulose 96-well microtiter (ELISPOT) plates were coated with an anti-IFNγ capture monoclonal antibody (Endogen, Rockford, Ill.). Cryopreserved PBMC, obtained at various times prior to or following vaccination, were thawed and cultured directly, i.e., without in vitro stimulation, in T-cell medium in these nitrocellulose microtiter (ELISPOT) plates at $2\times10^5$ cells/well. Cultures were allowed to proceed for 48 hours in media without antigen, with 2 µg/ml PAP protein (Research Diagnostics Inc., Flanders, N.J.), with 250 ng/ml tetanus toxoid (Calbiochem, San Diego, Calif.), or with 5 µg/ml phytohemagglutinin (PHA, positive mitogenic control, Fisher, Pittsburgh, Pa.). ELISPOT plates were then washed and probed for 1.5 hours with a biotinylated anti-IFNγ antibody (Endogen). After incubation, the wells were washed, incubated with streptavidin-labeled alkaline phosphatase for one hour, and then developed with BCIP/NBT colorimetric substrate (BioRad, Hercules, Calif.) for 15-30 minutes. The number of spots per well was determined with an automated ELISPOT reader and normalized to $10^6$ starting PBMC. The mean number of spots detected under media-only conditions at each time point was subtracted from the antigen-specific conditions to enumerate antigen-specific IFNγ spot-forming units (SFU)+/− standard deviation. Statistical analysis was performed using a two-tailed t test. A p value smaller than 0.05 was deemed statistically significant.

Results:

While some individuals develop PAP-specific IFNγ-secreting immune responses immediately after DNA vaccine immunization, such PAP-specific response could not be detected immediately in other individuals but became detectable several months after immunization. In this trial, eight of 22 patients had a greater than 200% increase in PSA doubling time, and this was significantly associated with the development of long-term PAP-specific IFNγ-secreting immune responses. One of these patients (ID007) is highlighted in FIG. 1, with panel A showing serum PSA levels and panel B showing the development of a durable PAP-specific IFNγ-secreting immune response. As shown in FIG. 1B, this patient eventually developed a PAP-specific immune response many months following immunization, yet he had no detectable immune response immediately following immunization. A similar finding of delayed T effector responses was also observed in two other patients who experienced a greater than 200% increase in PSA doubling time (ID005 and ID014).

While it is conceivable that an effector immune response might have taken months to develop, an alternative explanation is that PAP-specific effector T cell responses were augmented during vaccination, but that these T cells were restrained by a regulatory immune response concurrent with, or augmented by, immunization. To determine if individuals with a delayed response had developed regulatory responses that decrease over time, allowing for detection of effector responses, a trans vivo delayed-type hypersensitivity (TV-DTH) assay was used to measure DTH responses to defined antigens. As shown in FIG. 1C, three patients had baseline recall responses to tetanus toxoid that remained following a booster immunization (given prior to the priming PAP DNA immunization), yet PAP-specific TV-DTH immune responses were not detected either pre- or post-immunization. These findings are consistent with previously published results using standard T-cell proliferation and IFNγ ELISPOT assays. When a blocking antibody specific for CTLA-4 was co-administered, however, robust PAP-specific immune responses were uncovered in all three patients immediately post-immunization (FIG. 1C). Surprisingly, co-administration of blocking antibodies to the immunosuppressive cytokines IL-10 and TGF-β failed to uncover a PAP-specific effector response (FIG. 1C).

Figure 2:
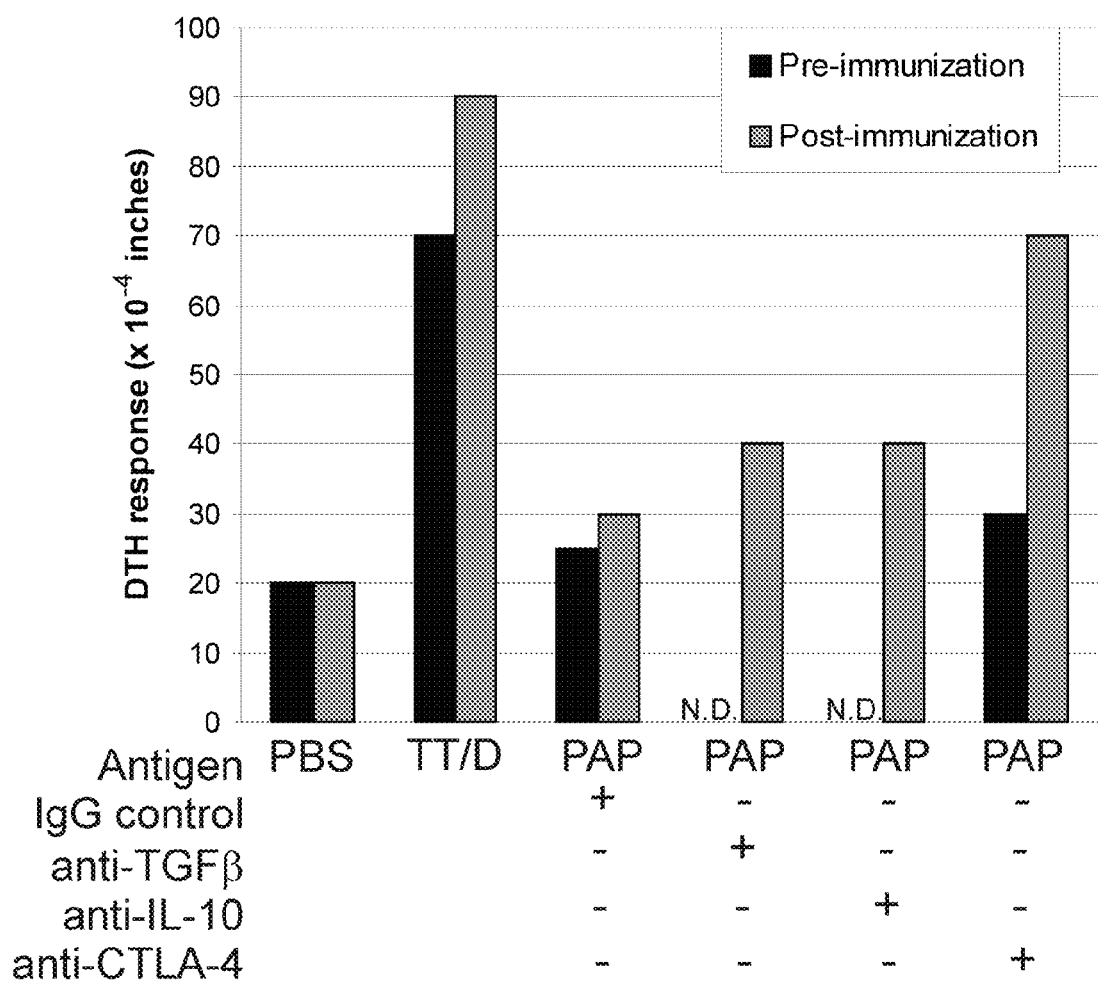
FIG. 2 illustrates DTH response prior to and following immunization with PAP DNA vaccination. Data shown are representative of two independent experiments. PAP=prostatic acid phosphatase; TT/D=tetanus toxoid; IgG control=antibody control; anti-TGF-β=antibody specific for transforming growth factor beta; anti-IL-10=antibody specific for interleukin 10; anti-CTLA-4=antibody specific for cytotoxic T-lymphocyte antigen 4; N.D.=not determined for the pre-treatment samples with anti-TGF-β or anti-IL-10 due to limited sample size.

A DTH response to the tetanus recall antigen, but not to the PAP antigen, was readily detectable in some individuals (FIG. 2; Table 1). Co-administration of a blocking antibody specific for CTLA-4 "uncovered" a response to PAP post-immunization (FIG. 2; Table 1, shaded boxes). Co-administration of blocking antibodies specific for the immunosuppressive cytokines IL-10 and TGF-β did not uncover a PAP-specific effector response (FIG. 2). One subject exhibited a CTLA-4-regulated response prior to immunization, but not after immunization (#4, Table 1). Approximately half of the individuals in whom CTLA-4-regulated responses were observed after immunization demonstrated evidence of effector T-cell responses, as evidenced by IFNγ-secretion, at subsequent time points following immunization (data not shown), suggesting that the detection of CTLA-4 regulated responses after immunization did not preclude detection of later effector cell function.

TABLE 1

| | Tetanus | | PAP | | | | | |
|---|---|---|---|---|---|---|---|---|
| | | | Pre-Immunization (Net DTH, in$^{-4}$) | | | Post-Immunization (Net DTH, in$^{-4}$) | | |
| Subject ID | Pre-Immunization (Net DTH, in$^{-4}$) | Post-Immunization (Net DTH, in$^{-4}$) | +IgG | +α-CTLA-4 | CTLA-4-Regulated PAP Response | +IgG | +α-CTLA-4 | CTLA-4-Regulated PAP Response |
| 02 | 40 | 50 | 10 | 0 | -10 | 10 | 30 | 20 |
| 03 | 50 | 50 | 30 | 20 | -10 | 30 | 30 | 0 |
| 04 | 40 | 40 | 10 | 30 | 20 | 20 | 12.5 | -7.5 |
| 05 | 30 | 40 | 10 | 10 | 0 | 5 | 20 | 15 |
| 06 | 40 | 30 | 20 | 20 | 0 | 20 | 50 | 30 |
| 07 | 50 | 70 | 5 | 10 | 5 | 10 | 50 | 40 |
| 08 | 40 | 45 | 25 | 25 | 0 | 25 | 20 | -5 |
| 09 | 80 | 70 | 30 | 40 | 10 | 35 | 35 | 0 |
| 10 | 60 | 60 | 25 | 27.5 | 2.5 | 30 | 15 | -15 |
| 11 | 40 | 30 | 10 | 10 | 0 | 0 | 2.5 | 2.5 |
| 12 | 40 | 30 | 10 | 20 | 10 | 5 | 0 | -5 |
| 13 | 30 | 40 | 30 | 30 | 0 | 30 | 20 | -10 |
| 14 | 30 | 40 | 10 | 20 | 10 | 10 | 27.5 | 17.5 |
| 15 | 60 | 50 | 20 | 20 | 0 | 35 | 10 | -25 |
| 16 | 25 | 35 | 10 | 10 | 0 | 5 | 30 | 25 |
| 17 | 40 | 40 | 10 | 10 | 0 | 5 | 20 | 15 |
| 18 | 50 | 55 | 20 | 20 | 0 | 5 | 15 | 10 |
| 19 | 25 | 30 | 20 | 20 | 0 | 20 | 30 | 10 |
| 20 | 40 | 35 | 30 | 40 | 10 | 5 | 15 | 10 |
| 21 | 50 | 40 | 20 | 20 | 0 | 10 | 0 | -10 |
| 22 | 70 | 60 | 10 | 12.5 | 2.5 | 12.5 | 27.5 | 20 |

EXAMPLE 2

Figure 3:
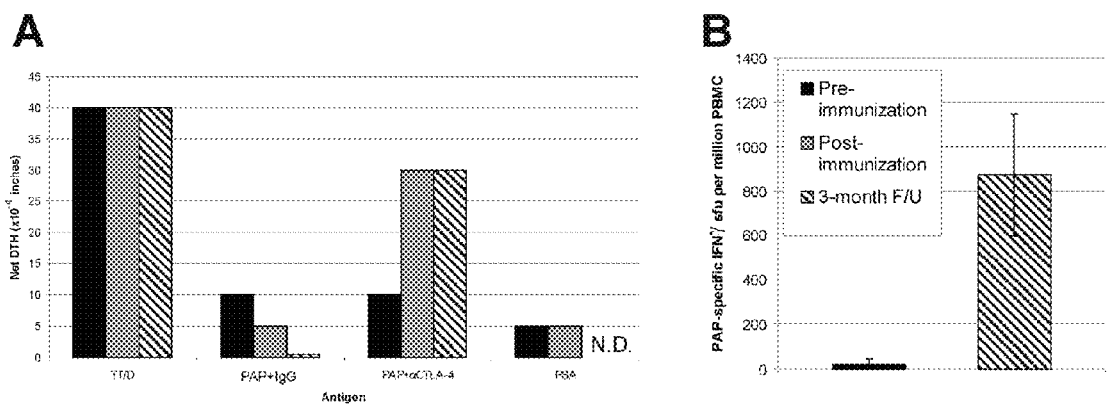
FIGS. 3A and B illustrate that CTLA-4-regulated DTH responses can persist.
FIG. 3B illustrates PAP-specific interferon gamma (IFNγ) secretion of PBMC at the indicated time points as determined by ELISPOT. The data are represented as mean and standard deviation of net PAP-specific IFNγ spot-forming units (SFU) per million PBMC.

Antigen-Specific CTLA-4 Regulation can Persist Several Months after Immunization To determine if the observed CTLA-4 regulation described in Example 1 was due to transient CTLA-4 expression on PAP-specific effector T cells or due to antigen-specific regulation of an effector response, PBMC from a patient who demonstrated a PAP-specific CTLA-4 regulated response were analyzed 3 months after immunization for a PAP-specific response. PBMC were obtained from the patient prior to immunization, two weeks after six biweekly immunizations, and three months following the post-immunization time point, as described in Example 1. PBMC were injected into the footpads of SCID mice with 1-25 μg of the antigens PAP or tetanus toxoid and blocking antibodies or control IgG (1

μg), as indicated. DTH responses were measured as net footpad swelling after 24 hours. CTLA-4 regulation could be observed three months after immunization (FIG. 3A). Also, PAP-specific effector response (IFNγ-secreting) was observable at this time (FIG. 3B). Antigen-specific regulation can occur by CD8+ cells, and is mediated through CTLA-4. The findings above suggested that the observed CTLA-4 regulation was not attributable to expression and suppression of effector cells alone, but rather to antigen-specific regulation of the effector responses.

Figure 4:
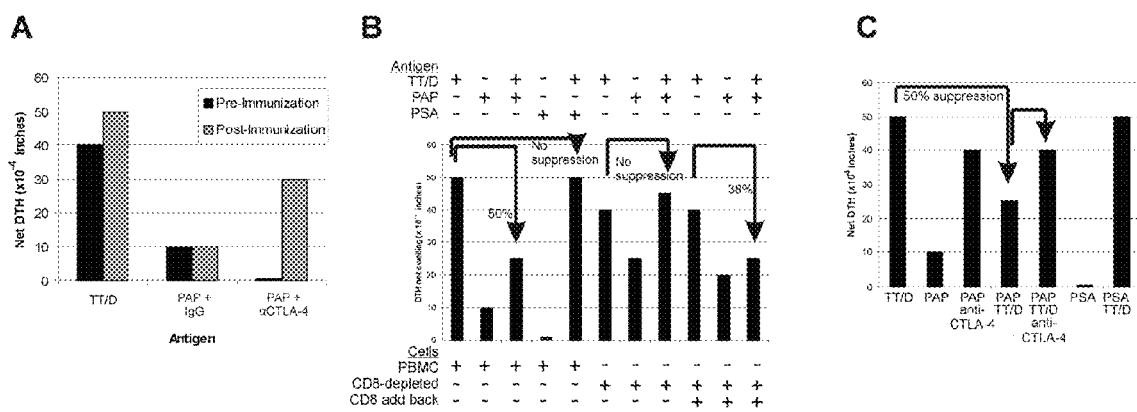
FIG. 4A-C illustrate that a CD8+ cell-mediated immune response specific for PAP suppresses a DTH response to a tetanus recall antigen.

To further characterize the cells responsible for this regulation, cells that raised PAP-specific regulatory responses were evaluated for their ability to suppress bystander DTH responses to tetanus toxoid. PBMC, obtained after immunization from an individual with a PAP-specific CTLA-4-regulated response detectable after immunization (#2, Table 1; FIG. 4A), were co-administered with PAP antigen, which led to suppression of a DTH response to the tetanus recall antigen. This suppression was specific for PAP, as suppression of DTH response to tetanus was not detectable with co-administration of another prostate-specific protein, PSA. Moreover, this response was CD8+ T-cell-dependent as depletion of CD8+ T-cells from PBMC, which did not affect the tetanus-specific DTH response, which is known to be CD4+ T-cell-mediated, abrogated expression. Furthermore, bystander suppression was restored with re-addition of purified CD8+ T-cells (FIG. 4B). The bystander suppression of DTH response to tetanus toxoid could also be abrogated by co-administering anti-CTLA-4 antibody (FIG. 4C).

EXAMPLE 3

Figure 5:
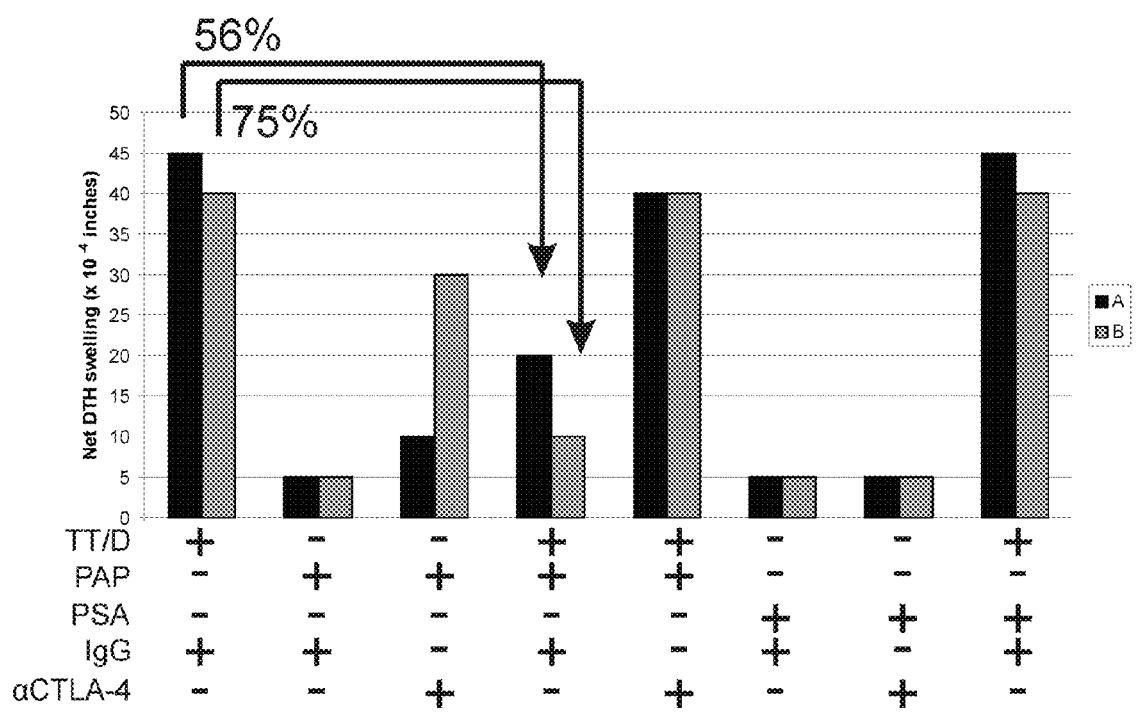
FIG. 5 illustrates that pre-existing PAP-specific immune regulatory responses suppress DTH responses to a recall antigen. Black bars=PBMC from patient A prior to immunization; grey bars=PBMC from patient B prior to immunization. Data shown are representative of two independent experiments.

CD8+ T Cell Immune Responses Specific for a Vaccine Antigen can Suppress a DTH Response to a Bystander Recall Antigen The experiments of Examples 1 and 2 evaluated PBMC obtained after immunization in individuals who otherwise showed no evidence of an effector immune response to PAP following immunization. To determine if this type of PAP-specific regulatory response was present prior to vaccination, TV-DTH assays were conducted essentially as described in Examples 1 and 2 to determine antigen-specific bystander suppression prior to vaccination. The tetanus recall antigen was injected into the footpads of SCID mice, essentially as described in Example 1, together with PBMC obtained prior to immunization from individuals who did not develop PAP-specific IFNγ-secreting immune responses after immunization, as determined by ELISPOT. The results demonstrate that these individuals showed evidence of PAP-specific bystander suppression of DTH responses to tetanus toxoid recall antigen (FIG. 5). However, there was no evidence of PSA-specific bystander suppression (FIG. 5). The bystander suppression of DTH responses to tetanus toxoid could be abrogated with a CTLA-4-blocking antibody (FIG. 5).

These results demonstrate that PAP-specific cells with bystander suppressor function were present in these individuals prior to vaccination.

This PAP-specific regulatory cell population was characterized by measuring bystander suppression in pre-immunization PBMC samples that had been depleted of specific T-cell populations. When CD8+ T cells were depleted, PAP-specific bystander suppression was lost and a tetanus-specific response could be detected (FIG. 6). Furthermore, when purified CD8+ T cells were added back to CD8-depleted PBMC, this PAP-specific bystander regulation was re-established. When CD8+ cells were MACS-sorted by the presence or absence of surface CTLA-4 expression, the addition of CD8+ CTLA-4+ cells to CD8-depleted PBMC restored the suppression of tetanus immune responses (FIG. 6), whereas the addition of CD8+CTLA-4− T cells did not. These data demonstrate that CD8+CTLA-4+ T cells comprise the PAP-specific immunosuppressive population.

EXAMPLE 4

CTLA-4 Blockade of PAP-Specific CD8+CTLA-4+ Regulatory Cells Decreases the Expression of Immunosuppressive Cytokine IL-35

Methods:
Protein Stimulations, Cell Sorting, RNA, cDNA, and Quantitative Real-time PCR: PBMC samples were stimulated for 24 hours with media alone (RPMI 1640 media supplemented with L-glutamine, penicillin, streptomycin, and 10% human AB serum), or either recombinant prostate specific antigen (PSA, 2 μg/mL, Chemicon) or recombinant human PAP (2 μg/mL, Chemicon) in the medium. Furthermore, PSA- or PAP-stimulated cultures were also treated with either a blocking antibody specific for CTLA-4 (clone AS32), or a murine IgG control. Cultures were collected, stained with antibodies specific for CD3, CD8, and CTLA-4, and sorted by flow cytometry (FACSAria, BD Biosciences), collecting the following populations: CD3+CD8+CTLA-4+, CD3+CD8+ CTLA-4− and CD3+CD8− (CD3: clone OTK3, eBioscience; CD8: clone SK1, eBioscience; CTLA-4: clone 14-D3, eBioscience). RNA was then collected from sorted cells using the Qiagen mRNA kit, and cDNA was reverse-transcribed with the iScript cDNA Synthesis kit (BioRad). The cDNA samples were then subjected to 40 cycles of amplification with primers specific for IL-12p35, IL-12p40, IL-23p19, IL-27p28, Ebi3, IL-10, or the ribosomal protein P0 as a control gene in a MyiQ@ Two-Color Real-Time PCR Detection System (Biorad) and were quantified by the comparative cycling threshold method. Fold induction results were analyzed by the $2^{-\Delta\Delta Ct}$ method relative to P0 expression and the media-only treatment group, and statistical differences between CTLA-4 and IgG-treated samples was performed using a two-tailed test, with $p \leq 0.05$ used to define a significant T-cell response.

Results:
While a crucial role for immunosuppressive cytokines such as IL-10 and TGF-β in mediating regulation in models of transplantation has been identified, no role for these cytokines was identified for the function of PAP-specific regulatory cells (data not shown). After discounting a primary role for these two cytokines in mediating bystander suppression, the potential contribution of IL-35 was explored. IL-35 is a recently identified anti-inflammatory cytokine that has been shown to be crucial to the suppressive function of CD4+ regulatory T cell responses. PBMC samples from a patient with a CTLA-4-regulated immune response (ID002) were stimulated for 24 hours with PAP in the presence of either CTLA-4 blocking antibody or an IgG control. As shown in FIG. 7A, stimulation with PAP resulted in a 20-30 fold induction in expression of IL-12p35 and Ebi3 subunits of IL-35 in CD8+CTLA-4+ T cells as compared to PSA-treated cells. Strikingly, when regulatory responses were inhibited using an anti-CTLA-4 antibody, the expression of the IL-35 subunits was significantly decreased in a PAP-specific fashion. PAP-specific IL-35 expression was not observed in CD3+CD8+ CTLA4− cells or in other T-cell populations (FIGS. 7B, 7C). Additionally, minimal expression of other components of the IL-12 family (IL-12p40, IL-23p19, and IL-27p28) was detected (FIG. 7). Such expression was unaffected by blockade of CTLA-4 (FIG. 7). Consistent with previous results, neither significant expression nor a CTLA-4-regulated decrease in expression of IL-10 was detected by quantitative real-time PCR (FIG. 7A), ELISA, or multiplex cytokine analysis (data not shown).

EXAMPLE 5

PAP-Specific CD8+ Regulatory Responses Mediate Suppression Via IL-35

Figure 8:
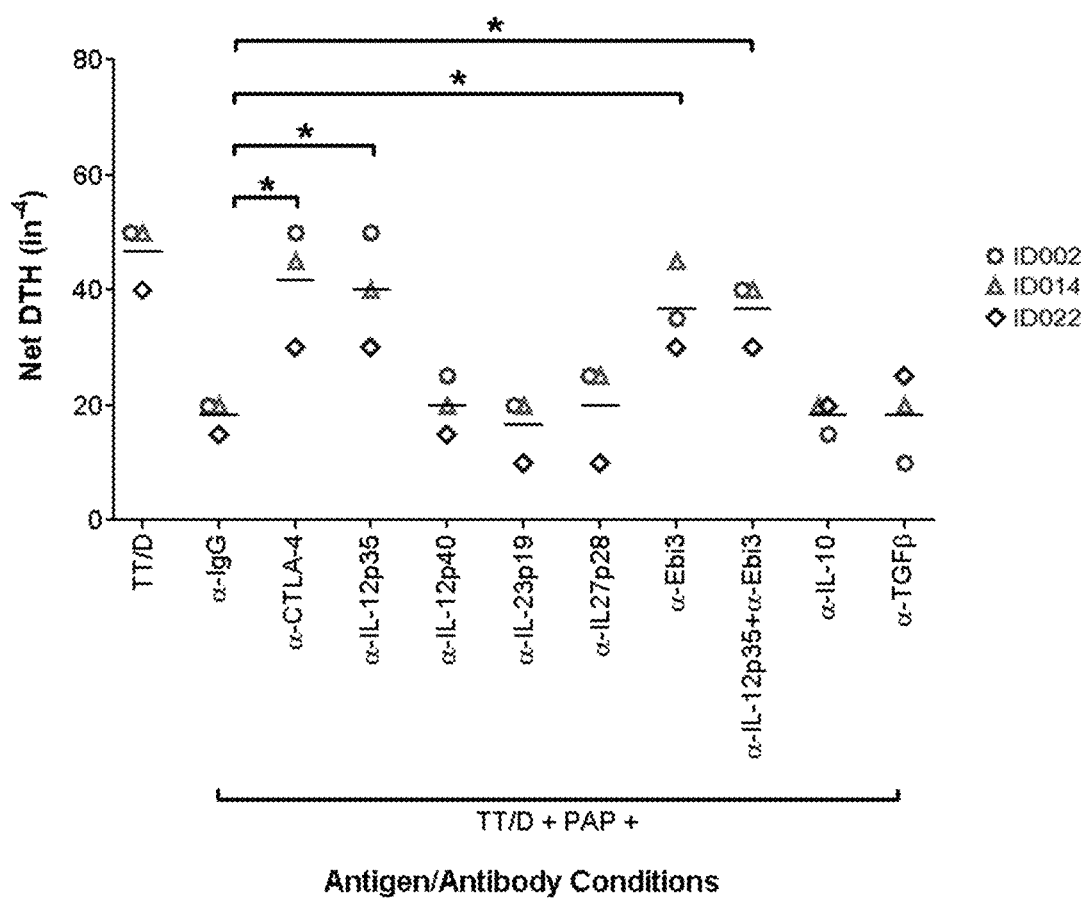
FIG. 8 illustrates suppression of PAP-specific regulatory response mediated by IL-35. Patients with CTLA-4-regulated PAP-specific bystander suppressive immune responses were stimulated with TT/D alone or TT/D and PAP in the presence of either an IgG control or blocking antibodies directed against CTLA-4, IL-12p35, IL-12p40, IL-23p19, IL-27p28, Ebi3, a combination of IL-12p35 and Ebi3 (both IL-35 subunits), IL-10, or TGF-β. Differences between treatment group mean DTH values (indicated by solid lines) were compared using a student's t-test with * indicating p<0.05.

After identifying PAP-specific IL-35 expression in CD8+ CTLA-4+ T cells, and after observing a decrease in this expression following inhibition of CTLA-4-mediated regulatory responses, the role of IL-35 in mediating PAP-specific suppressive responses was further examined. Samples from three patients with pre-existing PAP-specific CD8+CTLA-4+ regulatory responses were evaluated for bystander suppression in the presence of various blocking antibodies. Specific neutralization of IL-35 (by blocking either or both of the IL-35 subunits, IL-12p35 and Ebi3) significantly relieved the PAP-specific bystander suppression of tetanus immune response in three of three patients tested (FIG. 8). Treatment with blocking antibodies targeting the other members of the IL-12 family (IL-12p40, IL-23p19, or IL-27p28), as well as those blocking the immunosuppressive cytokines IL-10 and TGF-β, did not relieve this PAP-specific bystander suppression. These data illustrate that PAP-specific regulatory cells mediate suppression via CTLA-4 and IL-35.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for administering a prostate cancer vaccine to an individual having an antigen-specific suppressive immune response to the prostate cancer vaccine, the method comprising the step of administering to the individual the prostate cancer vaccine and an agent that suppresses an immunosuppressive function of at least one immune regulatory cell-associated molecule,
   wherein the agent is an antibody that suppresses an immunosuppressive function of IL-35, IL-12p35, Ebi3, or CTLA4, and
   wherein the antigen-specific suppressive immune response is characterized by the presence in the individual of $CD8^+/IL-35^+/CTLA-4^+$ T-lymphocytes.

2. The method of claim 1, wherein the antigen is prostatic acid phosphatase (PAP).

3. The method of claim 1, wherein the prostate cancer vaccine comprises a nucleic acid.

4. The method of claim 3, wherein the nucleic acid comprises a nucleotide sequence encoding the PAP antigen.

5. The method of claim 1, wherein the at least one immune regulatory cell-associated molecule is selected from the group consisting of IL-35, IL-12p35, Ebi3, and CTLA4.

* * * * *